United States Patent [19]
Grandjean et al.

[11] Patent Number: 5,496,353
[45] Date of Patent: Mar. 5, 1996

[54] END-OF-LIFE INDICATION SYSTEM FOR IMPLANTABLE PULSE GENERATOR

[76] Inventors: Pierre A. Grandjean, 61, Rue Albert Dekkers, Warsage, Belgium, 4608; Robert Leinders, Veersestraat 51, 6143 AM Guttecoven, Netherlands; Ivan Bourgeois, 9 Rue Jean Gome, Verviers, Belgium, 4802

[21] Appl. No.: 126,152

[22] Filed: Sep. 23, 1993

[51] Int. Cl.$^6$ .................................................. A61N 1/36
[52] U.S. Cl. ........................................................ 607/29
[58] Field of Search .............................. 607/29, 32, 16; 600/16

[56] References Cited

U.S. PATENT DOCUMENTS

| Re. 32,361 | 2/1987 | Duggan | 607/32 |
|---|---|---|---|
| 3,841,336 | 10/1974 | Daynard . | |
| 3,882,322 | 5/1975 | Gobeli . | |
| 4,120,307 | 10/1978 | Jirak et al. | 607/29 |
| 4,390,020 | 6/1983 | Herpers | 607/29 |
| 4,411,268 | 10/1983 | Cox | 128/421 |
| 4,686,990 | 8/1987 | Moberg | 128/419 PT |
| 4,813,952 | 3/1989 | Khalafalla | 623/3 |
| 5,069,680 | 12/1991 | Grandjean | 600/16 |

OTHER PUBLICATIONS

"Continued Studies in Prolonged Circulatory Support By Direct Mechanical Ventricular Assistance" by G. L. Anstadt and W. E. Britz, Jr., vol. XIV Trans. Amer. Soc. Artif. Int. Organs, 1968, pp. 297–303.

Primary Examiner—William E. Kamm
Assistant Examiner—Kennedy J. Schaetzle
Attorney, Agent, or Firm—Harold R. Patton

[57] ABSTRACT

An end-of-life (EOL) indicator for an implantable pulse generator (IPG)— especially of the neuromuscular stimulation variety—indicates an approaching battery EOL condition via an electrocardiogram (ECG) by changing the nature of the muscle stimulation burst signals. IPG internal circuitry detects an approaching EOL condition and modifies the burst signals by, for example, decreasing the number of pulses in a burst, increasing the heart contraction-to-powering-muscle contraction ratio, or alternating between two numbers of pulses in successive burst cycles. The approaching battery EOL condition can be easily ascertained via trans-telephonic monitoring by analyzing a transmitted ECG alone, for the above-mentioned burst signal changes. By observing the patterns in the ECG caused by the burst signal changes, a clinician could be aware of an approaching EOL without having known the original muscle stimulation burst signal parameters.

9 Claims, 5 Drawing Sheets

ECG $V_B > V_I$

MUSCLE OUTPUT

1) $V_B \leq V_I$

MUSCLE OUTPUT

2) $V_B \leq V_I$

FIG.5D

3) $V_B \leq V_I$

FIG.5E

END-OF-LIFE INDICATION SYSTEM FOR IMPLANTABLE PULSE GENERATOR

FIELD OF THE INVENTION

The present invention generally relates to battery end-of-life indicators for implantable pulse generators-especially those suitable for neuromuscular stimulation.

BACKGROUND OF THE INVENTION

Muscle-powered cardiac assist systems been developed to aid patients with chronically and unacceptably low cardiac output, and who cannot have their cardiac output raised to acceptable levels by traditional treatments such as drug therapy. (See G. L. Anstadt & W. E. Britz, Jr., *Continued Studies in Prolonged Circulatory Support by Direct Mechanical Ventricular Assistance*, 14 Trans. Amer. Soc. Artif. Int. Organs 297 (1968)). U.S. Pat. No. 4,813,952 issued to Khalafalla, which is hereby incorporated by reference, teaches a cardiac assist system powered by surgically modified muscle tissue, such as the latissimus dorsi flap, using cardiomyoplasty techniques. Being fast twitch muscle tissue, the latissimus dorsi can be converted to slow twitch tissue for efficient long-term use by using the techniques taught in U.S. Pat. No. 4,411,268 issued to Cox, and also hereby incorporated by reference.

In a system using muscle wrapped about an ailing heart, an implantable pulse generator (IPG) senses contractions of a heart via one or more sensing leads, and stimulates the appropriate nerves of the muscle tissue (via stimulation leads) to cause the muscle tissue to contract in synchrony with the heart chamber of interest. As a result, the heart is made to contract more forcefully, raising the stroke volume, and hence cardiac output.

IPGs typically include end-of-life (EOL) indication circuitry for detecting and indicating an approaching depleted battery state. In prior art cardiac pacemakers, a typical response to an EOL condition is to lower the pacing rate.

A special EOL indication signal can be transmitted transtelephonically from the IPG (whether cardiac, neuromuscular, etc.) when the patient is at a remote location. However, this requires specific special equipment at the receiver end to properly interpret the signal as an EOL signal. Thus, without the special equipment, a clinician interpreting the transtelephonic data would not know that an EOL condition is imminent, and would not then be able to advise the patient that the time for replacement of the IPG has arrived.

SUMMARY OF THE INVENTION

The following are objects of the present invention in view of the above.

A first object of the present invention is to provide a battery EOL indicator for an IPG which is functional via transtelephonic monitoring, and without the need for a special receiver/programmer.

A second object of the present invention is to provide a battery EOL indicator for an IPG which indicates an approaching EOL condition without the need to make reference to stimulation signal parameters.

A third object of the present invention is to provide an IPG with a battery EOL indicator in which current consumption is reduced upon an indication of an approaching EOL condition, thus increasing the effective operation time of the unit.

A fourth object of the present invention is to provide a neuromuscular stimulation IPG capable of meeting all of the above objects.

There is provided in accordance with the present invention, a pacemaker system at least including:

an IPG at least including stimulation pulse generator means, battery EOL monitoring means for detecting an approaching battery EOL condition, and stimulation pulse generator modifier means coupled to the stimulation pulse generator means for intelligently modifying stimulation pulse signals generated by the stimulation pulse generator; and a battery EOL condition indicator means coupled to the EOL monitoring means and to the stimulation pulse generator modifier means;

wherein, upon the detection of an approaching battery EOL condition, the EOL condition indicator means activates the stimulation pulse generator modifier means, and the stimulation pulse signals form discernible patterns indicating the approaching EOL condition, without reference to stimulation pulse signal parameters.

In an IPG at least including stimulation pulse generator means, and telephonic signal generator means coupled to the stimulation pulse generator means adapted to transmit an ECG, there is provided in accordance with the present invention, a battery EOL condition indicator at least including:

battery EOL monitoring means for detecting an approaching battery EOL condition; and stimulation pulse generator modifier means coupled to the stimulation pulse generator means for intelligently modifying stimulation signals output by the stimulation pulse generator;

wherein, upon the detection of an approaching battery EOL condition, the ECG is modified to display discernible patterns indicating the approaching EOL condition, without reference to stimulation pulse signal parameters.

And, there is also provided in accordance with the present invention, a battery EOL condition indication method for an IPG at least including stimulation pulse generator means for generating stimulation pulse signals, the method at least including the steps of:

detecting an approaching battery EOL condition; and intelligently modifying stimulation signals output by the stimulation pulse generator;

wherein, upon the detection of an approaching battery EOL condition, the stimulation pulse signals form to display discernible patterns indicating the approaching EOL condition, without reference to stimulation pulse signal parameters.

The details of the present invention will be revealed in the following description, with reference to the attached drawing.

BRIEF DESCRIPTION OF THE DRAWING

The various figures of the drawing are briefly described as follows:

FIG. 5D is an EG of muscle stimulation bursts of a second embodiment of the present invention corresponding to the ECG in FIG. 5A, after the detection of an approaching EOL condition.

FIG. 5E is an EG of muscle stimulation bursts of a third embodiment of the present invention corresponding to the ECG in FIG. 5A, after the detection of an approaching EOL condition.

DETAILED DESCRIPTION OF THE PREFERRED EMBODIMENTS

The present invention employs a sensor to monitor cardiac electrical activity and cardiac demand in a skeletal muscle-powered cardiac assist system (CAS). A basic CAS may be configured in a variety of ways as described in the aforementioned patent to Khalafalla. Several of these configurations are discussed herein by way of illustration, and are not intended to limit the present invention.

Figure 1:
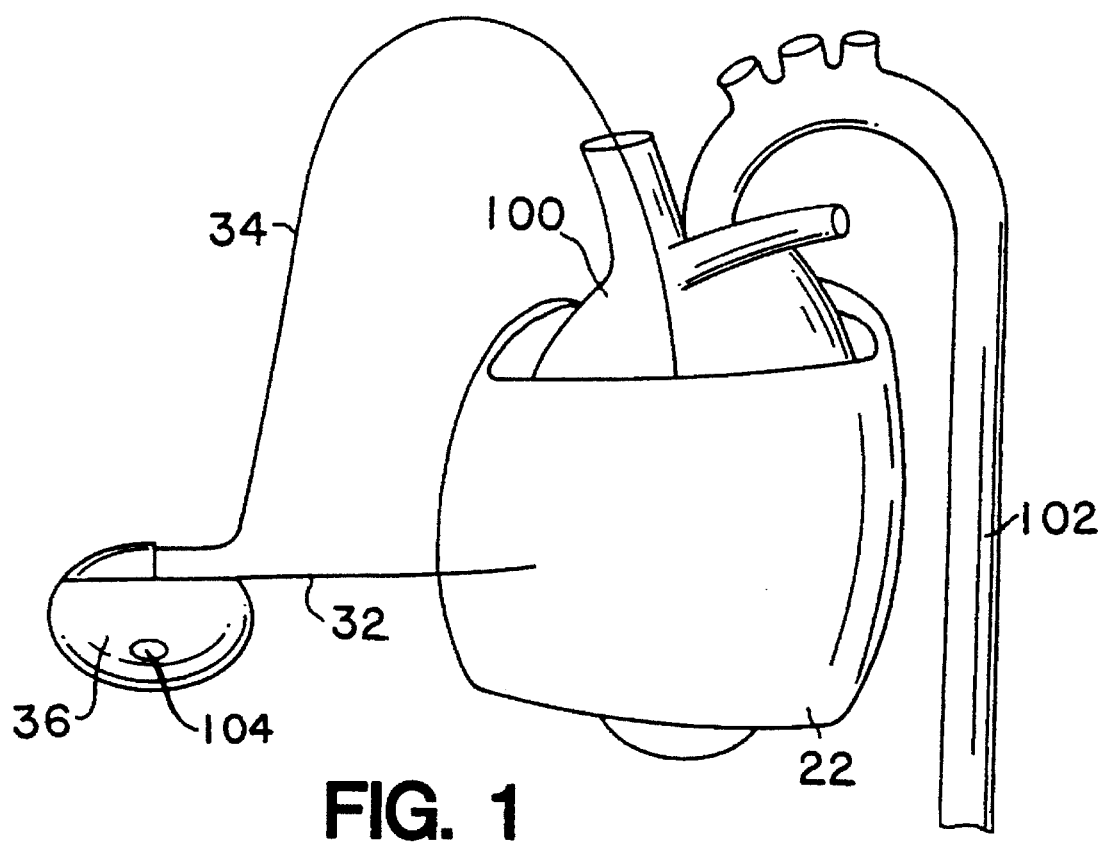
FIG. 1 is a first embodiment of a cardiac assist system capable of use with the present invention, wherein the skeletal muscle is wrapped about the myocardium

FIG. 1 is an embodiment of the present invention wherein skeletal muscle 22 is wrapped about a human heart 100. Skeletal muscle 22 is conditioned as a slow twitch muscle according to the aforementioned patent to Cox. An IPG 36 is coupled to a pacing lead 34 to produce a demand pacemaker. In addition, the IPG 36 stimulates skeletal muscle 22 to contract in synchrony with the heart 100. The simultaneous contraction of the skeletal muscle 22 provides assistance to the heart 100 to increase its systolic pressure in the descending aorta 102 and elsewhere in the circulatory system.

According to the present invention, the IPG 36 employs an activity sensor 104 to, in addition to sensing cardiac activity via the pacing lead 34, sense and output indicia of the patient's activity, and hence cardiac demand.

Figure 2:
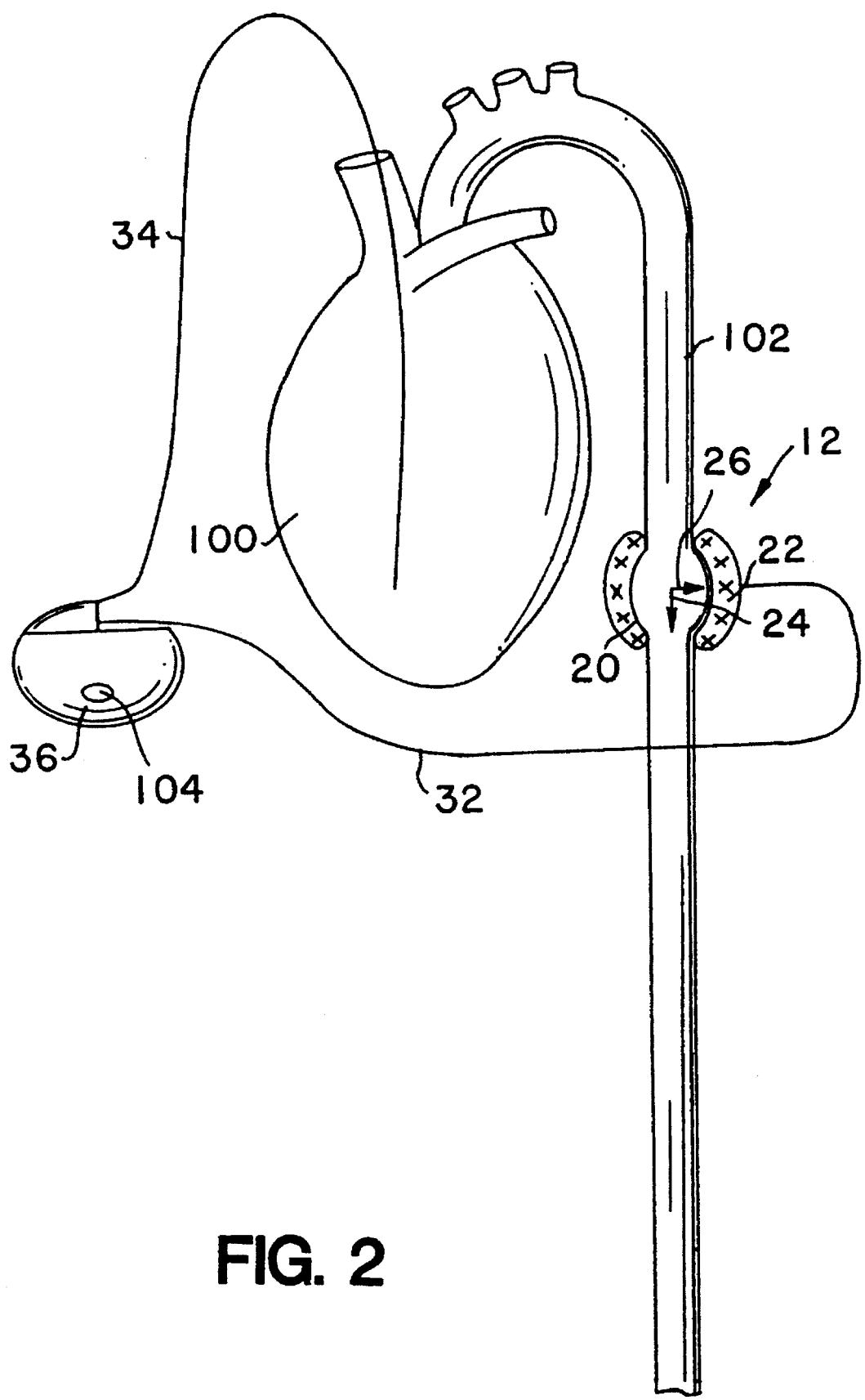
FIG. 2 is an alternative embodiment of a cardiac assist system capable of use with the present invention, wherein the skeletal muscle is wrapped about the descending aorta.

FIG. 2 is an alternate embodiment of the CAS in FIG. 1. In this embodiment, skeletal muscle 22 is wrapped about an artificial chamber 20, which chamber is inserted in series with the descending aorta 102. Unlike the embodiment in FIG. 1, the IPG 36 stimulates the skeletal muscle 22 to contract following evacuation of the heart 100, which is accomplished by the insertion of a delay between a paced or sensed beat of the heart 100 and the stimulation of the skeletal muscle 22 as discussed infra.

Figure 3:
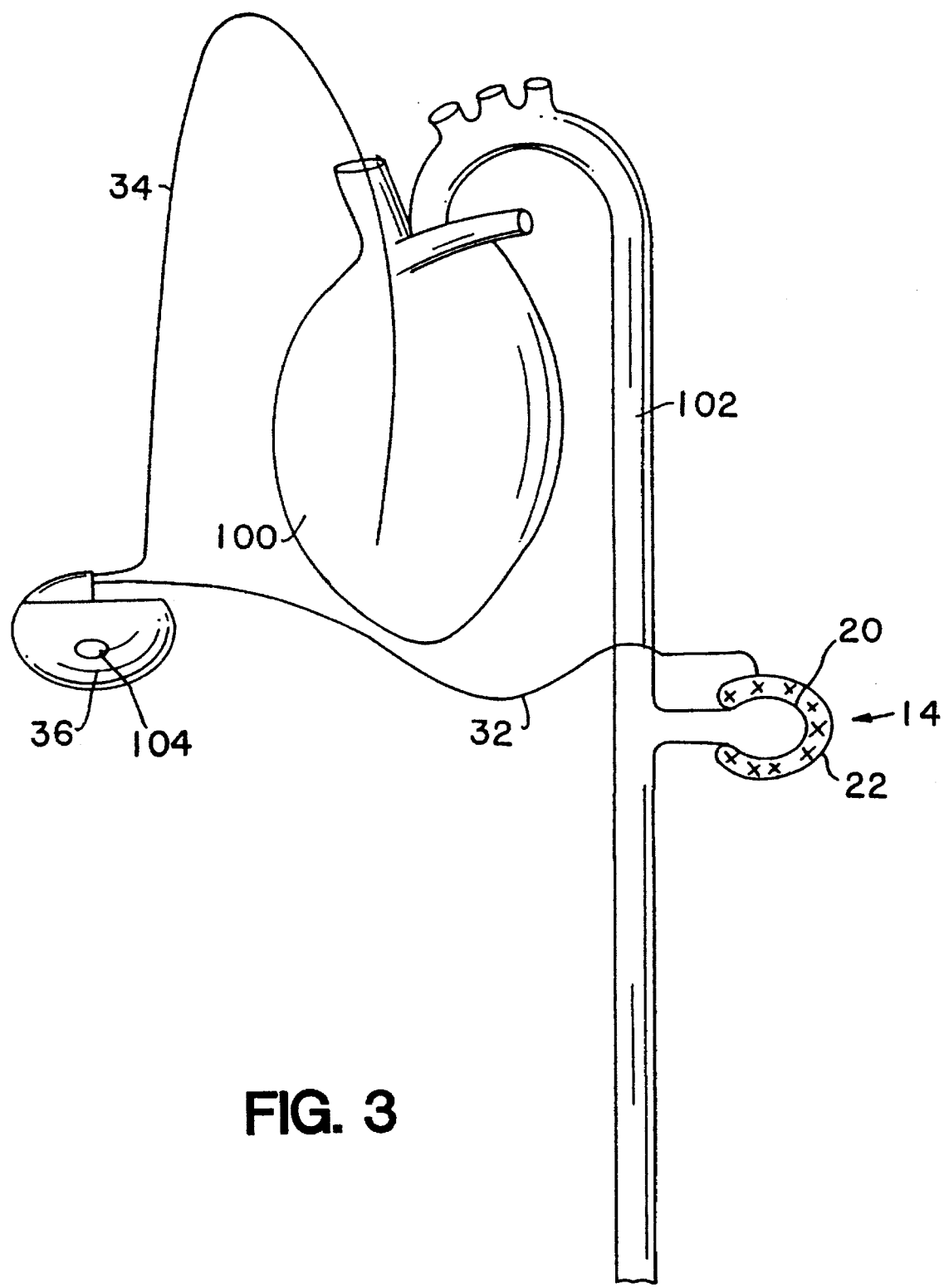
FIG. 3 is yet another alternative embodiment of a cardiac assist system capable of use with the present invention, wherein the skeletal muscle performs counter-pulsation of the descending aorta.

FIG. 3 is another alternate embodiment of the CAS in FIG. 1 wherein an artificial chamber 20 is coupled external to the descending aorta 102. In this configuration the skeletal muscle 22 is stimulated to counter-pulse the heart 100, which raises its diastolic pressure, thereby increasing its perfusion. This is accomplished by the generation of sufficient delay by the IPG 36, between and sensed or paced contraction of the heart 100 and stimulation of the skeletal muscle 22 to cause the desired counter-pulsation.

Figure 4:
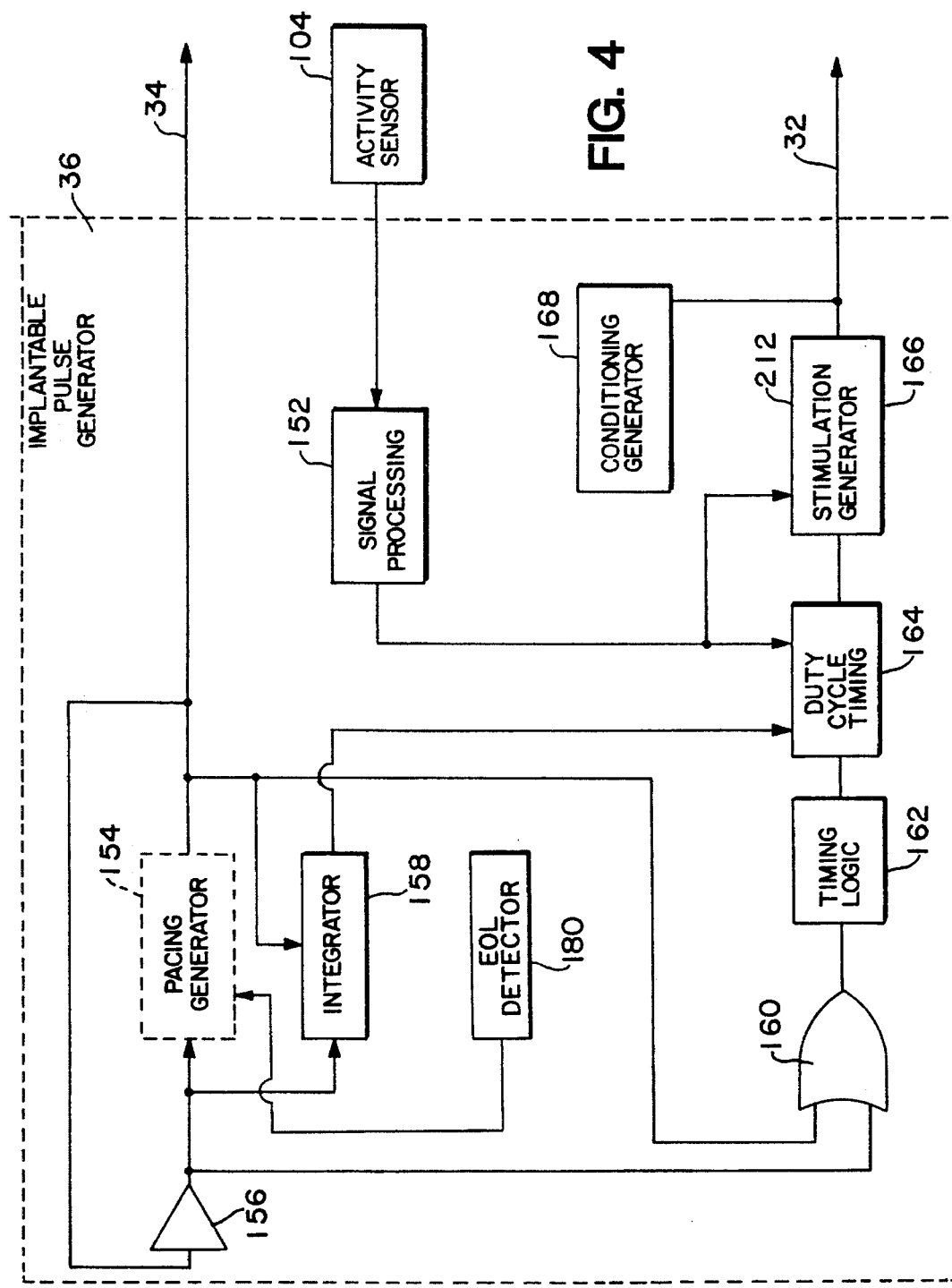
FIG. 4 is a block diagram of the IPG of the present invention.

FIG. 4 is a schematic block diagram of the IPG of the present invention. It includes a demand pacing generator 154 as is known in the art. In operation, the electrical activity of the patient's heart is monitored via the pacing lead 34. A sense amplifier 156 detects any naturally occurring heart depolarization (representing a contraction), and notifies the pacing generator 154. If the natural depolarization is sensed within an allotted time, the output of the pacing generator 154 is inhibited. However, if the pacing generator 154 determines that sufficient has elapsed since the previous depolarization, it generates a pacing pulse to the heart via the pacing lead 34 to artificially stimulate the heart 100 to contraction.

A stimulation generator 166 generates a burst of pulses in a manner known in the art to cause contraction of the skeletal muscle 22 in the proper timing relation to the contraction of the heart 100. Accordingly, an OR-gate 160 produces an output whenever the sense amplifier 156 senses a naturally occurring contraction, or whenever the pacing generator 154 generates a pacing pulse. The output of the OR-gate 160 enables timing logic 162, which generates a desired amount of delay. The delay is nearly zero for the embodiment of FIG. 1 because maximum assistance to the heart 100 is provided when the skeletal muscle 22 contracts in synchrony with the heart.

The embodiment of FIG. 2 requires a longer delay, on the order of one-half the cardiac cycle (i.e., the R-to-R interval). The embodiment of FIG. 3 requires yet a longer delay, being somewhat greater than one-half the cardiac cycle. This is necessary because that embodiment is intended to increase diastolic pressure in the aorta.

The output of the timing logic 162 is a timing pulse timed according to the specific embodiment (e.g., FIGS. 1, 2 or 3). The timing pulse is supplied to a duty cycle timing circuit 164, which is a variable digital counter producing an output corresponding to a variable number of pulses received from the timing logic 162. The normal output of the duty cycle timing circuit 164 is one pulse for each pulse received from the timing logic 162, corresponding to one-for-one stimulation of skeletal muscle rate compared to the cardiac rate. It should be understood that a lower rate is possible.

Overall cardiac rate is determined by an integrator 158, which receives input signals from both the sense amplifier 156 and the pacing generator 154, representing naturally occurring contractions and paced contractions, respectively. The integrator 158 produces an average current heart rate, which is used by the duty cycle timing circuit 164 to adjust its variable rate counter.

The output from the duty cycle timing circuit 164 controls the generation, vel non, of muscle stimulation pulses from a stimulation generator 166 via a stimulation lead 32. The pulses from the stimulation generator 166 typically form a series of bursts needed for neuromuscular stimulation.

Activity signals from the activity sensor 104 are processed by a signal processing circuit 152 to filter out noise and other unwanted components. The processed activity signals modulate the duty cycle timing circuit 164 and the stimulation generator 166, so as to change the burst rate and number of burst pulses in accordance with anticipated cardiac demand.

In accordance with the present invention, an EOL detector 180 detects an approaching EOL condition of the IPG batteries (not shown), in any one of a number of ways well known in the art, such as disclosed in U.S. Pat. No. 3,841,336 issued to Daynard, and U.S. Pat. No. 3,882,322 issued to Gobeli, to name just two. The aforementioned letters patents are hereby incorporated by reference. The EOL detector 180 sends an EOL signal to the pacing generator 154, which according to a pre-programmed protocol can cause the number of pulses in a burst to be reduced, cause the synchronization ratio (number of cardiac contractions compared to the number of powering muscle contractions) to increase, or a combination of the two.

Figure 5A:
FIG. 5A is a sample electrocardiogram (ECG).
Figure 5B:
FIG. 5B is an electrogram (EG) of muscle stimulation bursts corresponding to the ECG in FIG. 5A, prior to the detection of an approaching EOL condition.

FIG. 5A is an ECG of a muscle-assisted heart, absent the corresponding muscle stimulation burst signals. In actuality, the resulting ECG of a CAS using cardiomyoplasty, for example, would be expected to contain indicia of the muscle stimulation burst signals. As such, FIGS. 5B–5E are merely convenient representations of possible muscle stimulation burst signals which may occur at the same time as the partial ECG in FIG. 5A. FIG. 5B is a representation of a standard muscle stimulation burst signal pattern for the powering muscle tissue before the battery voltage $V_B$ reaches the EOL indication level $V_I$.

The ECG is transtelephonically transmitted from the patient's remote location to a clinician's receiver and display monitor by a device (not shown) external to the IPG in the preferred embodiment. In an alternate embodiment, a telemetered signal generated from within the IPG could transmit the ECG when the muscle pacing artifact cannot be seen very well, for example.

Figure 5C:
FIG. 5C is an EG of muscle stimulation bursts of a first embodiment of the present invention corresponding to the ECG in FIG. 5A, after the detection of an approaching EOL condition.

In response to an EOL signal from the EOL detector 180 (i.e., $V_B \leq V_1$), the IPG 36 changes the muscle stimulation burst signals from the standard pattern shown in FIG. 5B to any of the patterns shown in FIGS. 5C–5E (all corresponding in time to the ECG in FIG. 5A), or combinations thereof. In FIG. 5C the muscle stimulation burst signals have a reduced number of pulses in the burst. In that example, the number of pulses is halved by reducing them from four in FIG. 5B to two. A clinician viewing a telephonically transmitted ECG would expect the muscle stimulation burst signal to appear as shown in FIG. 5B. Therefore, any discernible departure from a typical muscle stimulation burst signal is an indication of the EOL condition, and is readily apparent to a clinician viewing the ECG alone, without the need for special circuitry. So, the drop in the number of burst pulses in FIG. 5C is a clear indication that the EOL condition is approaching.

As an alternative to the response represented by FIG. 5C, the synchronization ratio can be increased. Thus, in FIG. 5D the number of burst pulses remains standard (the same as in FIG. 5B), but the synchronization ratio changes from 1-to-1 to 2-to-1. This would be another form of an EOL indication to the clinician.

In yet another alternative to the EOL indication pattern, the burst pulses can alternate between two different numbers on alternate cycles. Thus, in FIG. 5E, the number of burst pulses alternates between four and two.

With further battery depletion, the number of burst pulses can be further reduced, and the synchronization ratio can be further raised, and the amount of change in these parameters can be made to be proportional to the amount of battery depletion.

In addition to providing a simple EOL indicator, the present invention also results in reduced battery current consumption, thus prolonging the before-replacement useful battery life.

Variations and modifications to the present invention may be possible given the above disclosure. However, all such variations and modifications are intended to be within the scope of the invention claimed by this letters patent. For example, the present invention is intended for use with therapeutic pulse generators in general, and not necessarily limited to muscle stimulators.

Additional changes to the stimulation bursts, and hence the EGG, could be used to indicate further battery voltage depletion after the EOL condition is reached. For example, the number of pulses in the burst is not only an indication of the EOL condition (when less than the full number are included in each burst), but is also proportional to the battery voltage, with further reductions in pulse number indicating further reduction in the battery voltage. The synchronization ratio can be varied in a similar (but opposite in the preferred embodiment) manner.

The present invention could also be manually triggered by a magnet to transmit an ECG which indicates the battery voltage by the presence, vel non, and magnitude of the previously-mentioned muscle pacing artifact pattern changes.

We claim:

1. A pacemaker system comprising:

an implantable pulse generator (IPG) comprising stimulation pulse generator means, battery end-of-life (EOL) monitoring means for detecting an approaching battery EOL condition, and stimulation pulse generator modifier means coupled to said stimulation pulse generator means for intelligently modifying stimulation pulse signals generated by said stimulation pulse generator wherein said IPG monitors cardiac stimulation signals and generates muscle stimulation bursts, and said stimulation pulse generator modifier means modifies a synchronization ratio between said cardiac stimulation signals and said muscle stimulation bursts; and a battery end-of-life (EOL) condition indicator means coupled to said EOL monitoring means and to said stimulation pulse generator modifier means;

wherein, upon the detection of an approaching battery EOL condition, said EOL condition indicator means activates said stimulation pulse generator modifier means, and said stimulation pulse signals form discernible patterns indicating said approaching EOL condition, without reference to stimulation pulse signal parameters.

2. The pacemaker system in claim 1 wherein said IPG is adapted to at least monitor cardiac stimulation signals and generate muscle stimulation bursts, and said stimulation pulse generator modifier means modifies the number of pulses in said stimulation bursts when activated.

3. The pacemaker system in claim 2 wherein said stimulation pulse generator modifier means is adapted to further modify the number of pulses in said stimulation bursts when the voltage of a subject battery is further reduced beyond an EOL condition.

4. The pacemaker system in claim 1 wherein said stimulation pulse generator modifier means is adapted to further modify said synchronization ratio when the voltage of a subject battery is further reduced beyond an EOL condition.

5. In an implantable pulse generator (IPG) comprising stimulation pulse generator means, and telephonic signal generator means coupled to said stimulation pulse generator mean adapted to transmit an electrocardiogram (ECG), a battery end-of-life (EOL) condition indicator comprising:

battery EOL monitoring means for detecting an approaching battery EOL condition; and stimulation pulse generator modifier means coupled to said stimulation pulse generator means for intelligently modifying stimulation signals output by said stimulation pulse generator wherein said IPG monitors cardiac stimulation signals and generates muscle stimulation bursts and said stimulation pulse generator modifier means modifies a synchronization ratio between said cardiac stimulation signals and said muscle stimulation bursts;

wherein, upon the detection of an approaching battery EOL condition said ECG is modified to display discernible patterns indicating said approaching EOL condition, without reference to stimulation pulse signal parameters.

6. The battery EOL condition indicator in claim 5 wherein said IPG is adapted to at least monitor cardiac stimulation signals and generate muscle stimulation bursts, and said stimulation pulse generator modifier means modifies the number of pulses in said stimulation bursts when activated.

7. The battery EOL condition indicator in claim 6 wherein said stimulation pulse generator modifier means is adapted to further modify the number of pulses in said stimulation bursts when the voltage of a subject battery is further reduced beyond an EOL condition.

8. The battery EOL condition indicator in claim 5 wherein said stimulation pulse generator modifier means is adapted to further modify said synchronization ratio when the voltage of a subject battery is further reduced beyond an EOL condition.

9. An implantable pulse generator comprising:

a stimulation pulse generator for generating muscle stimulation bursts and cardiac pacing pulses in a predefined ratio;

a battery end-of-life monitor for detecting an approaching end-of-life condition for a battery; and a stimulation pulse modifier coupled to the stimulation pulse generator and the battery end-of-life monitor, the stimulation pulse modifier modifying the predefined ratio of muscle stimulation bursts and cardiac pacing pulses upon detection of the approaching end-of-life condition.

* * * * *